(12) United States Patent
Parris

(10) Patent No.: US 6,273,874 B1
(45) Date of Patent: Aug. 14, 2001

(54) PROTECTED PEELABLE U-WING INTRODUCER

(75) Inventor: Wayne Parris, Anaheim, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/376,999

(22) Filed: Aug. 18, 1999

(51) Int. Cl.[7] .................................................. A61M 5/178
(52) U.S. Cl. ................ 604/198; 604/164.08; 604/164.05
(58) Field of Search .......................... 604/164.01–164.08, 604/165.01–165.03, 177, 187, 192, 198

(56) References Cited

U.S. PATENT DOCUMENTS

| | | | |
|---|---|---|---|
| 3,359,978 | 12/1967 | Smith, Jr. ........................... | 128/214.4 |
| 3,382,872 | 5/1968 | Rubin ................................ | 128/214.4 |
| 3,766,915 | 10/1973 | Rychlik ............................. | 128/214.4 |
| 4,147,165 | 4/1979 | Tauschinski ....................... | 128/214.4 |
| 4,269,186 | * 5/1981 | Loveless et al. ................... | 128/214.4 |
| 4,306,562 | 12/1981 | Osborne ............................ | 128/348 |
| 4,377,165 | 3/1983 | Luther et al. ...................... | 128/214.4 |
| 4,411,654 | 10/1983 | Boarini et al. ..................... | 604/165 |
| 4,449,973 | 5/1984 | Luther ............................... | 604/161 |
| 5,120,320 | * 6/1992 | Fayngold .......................... | 604/177 |
| 5,489,273 | 2/1996 | Whitney et al. . | |
| 5,971,957 | 10/1999 | Luther et al. . | |

FOREIGN PATENT DOCUMENTS

| | | | |
|---|---|---|---|
| 528271 | 11/1972 | (CH) | ..................................... 654/72 |
| 0 366 336 | 2/1990 | (EP) . | |
| WO 88/03035 | 5/1988 | (WO) . | |

* cited by examiner

Primary Examiner—Anhtuan T. Nguyen
Assistant Examiner—Ann Y. Lam
(74) Attorney, Agent, or Firm—Eric M. Lee

(57) ABSTRACT

A protected peelable introducer for insertion into an anatomical passageway such as a vein or artery. The introducer comprises a needle assembly having a U-wing member and a stylet in fluid communication with the U-wing member that defines a sharpened distal tip. Additionally, the introducer includes a protective sheath cooperatively engaged to the U-wing member of the needle assembly. The sheath is movable relative to the U-wing member from a non-operative position whereat the distal tip is exposed to an operative position whereat the distal tip is covered by the sheath. Furthermore, the sheath is separable into two halves such that when the needle assembly is divided into two halves, the sheath covers the sharpened distal tips of the separated stylet. Therefore, upon separation of the needle assembly, the sheath protects health care workers from inadvertent needle sticks caused by the sharpened distal tip of the stylet.

7 Claims, 2 Drawing Sheets

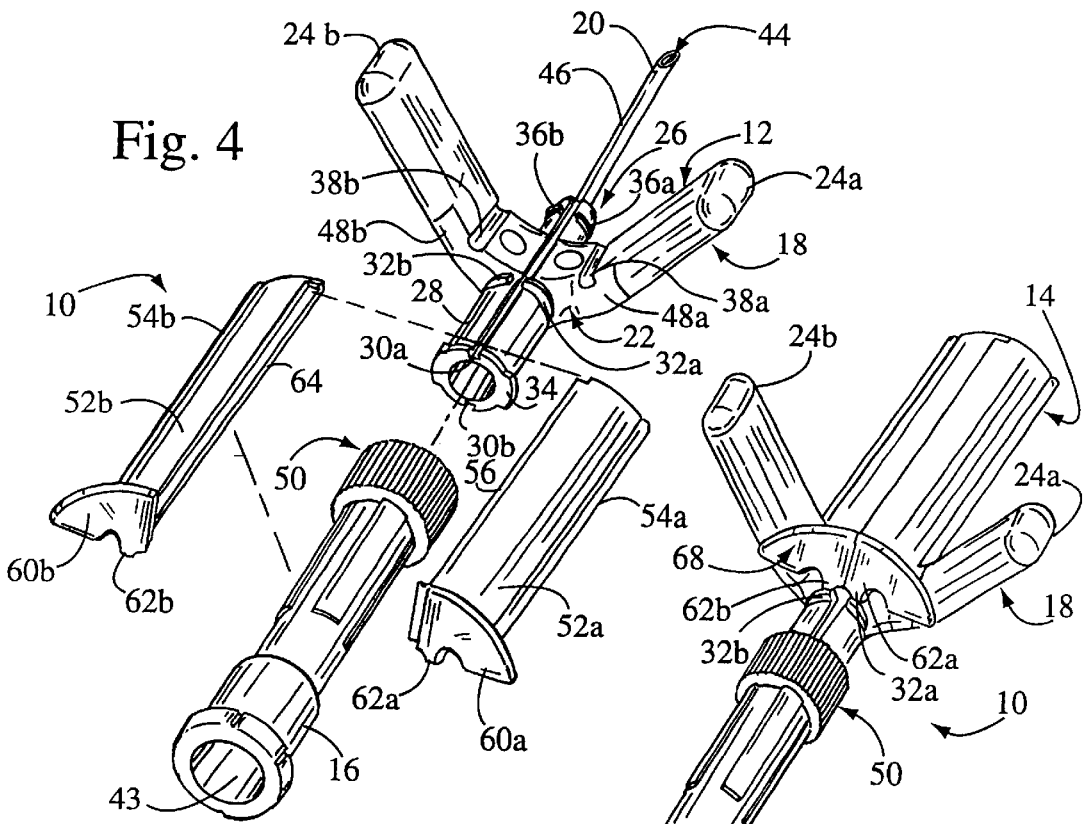
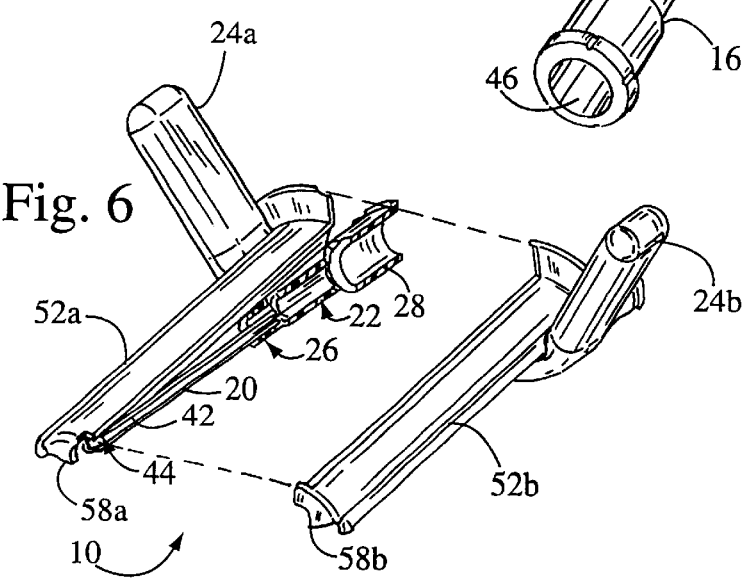

PROTECTED PEELABLE U-WING INTRODUCER

CROSS-REFERENCE TO RELATED APPLICATIONS (Not Applicable)

STATEMENT RE: FEDERALLY SPONSORED RESEARCH/DEVELOPMENT (Not Applicable)

BACKGROUND OF THE INVENTION

The present invention generally relates to medical devices, and more particularly to a peelable introducer that prevents inadvertent needle sticks.

In the medical arts, catheters are used to deliver medicament to a prescribed location within a patient's body. Such catheters are inserted into the lumen of an anatomical passageway (e.g., an artery or vein) with a peelable introducer. Typically, the introducer comprises a tubular piercing stylet with a beveled distal tip. The stylet is formed with two weakened areas along a longitudinal axis thereof. Additionally, attached to a proximal end of the stylet are two tab members that facilitate tearing of the stylet along the weakened areas, as will be further explained below. A flash chamber is removably attached and in fluid communication with the proximal end of the stylet. The flash chamber is fabricated from a translucent material and contains a hollow interior such that fluid (e.g. blood) flowing into the distal tip of the stylet is detected within the interior of the chamber.

The introducer is used by piercing the artery or vein with the distal tip of the stylet and thereby advancing such into the artery or vein of the patient. A proper insertion of the stylet into the vein or artery of the patient is indicated when blood is detected in the flash chamber. After blood is detected, the flash chamber is removed from the proximal end of the stylet and the catheter is then inserted into the stylet and snaked through the patient's artery or vein until the distal end of the catheter is in a desired location within the patient's body. Once the catheter is in a desired location, the introducer is removed from within the blood vessel of the patient and torn along the weakened areas into two halves with the tab members to remove the stylet from the catheter. As a result of the tearing of the introducer, the stylet is separated into two halves which are unprotected and can lead to inadvertent needle trauma to health care workers.

Increasingly, health care workers are at a risk of inadvertent needle trauma (i.e., needle sticks) when handling needles with sharpened tips. In recent years, such inadvertent needle trauma has become a cause for heightened concern in view of the increase in the incidents of serious or potentially fatal blood-born pathogens such as human immunodeficiency virus (HIV) and the hepatitis B virus. Therefore there exists an ongoing motivation to provide safety devices and apparatus for preventing health care workers from incurring inadvertent needle trauma when handling sharpened needles.

The present invention provides a peelable introducer which prevents inadvertent needle trauma after removal from the patient. In this respect, the present invention protects the health care worker by covering the tips of the stylet after removal from the patient and separation into two halves.

BRIEF SUMMARY OF THE INVENTION

In accordance with the preferred embodiment of the present invention there is provided a peelable introducer for insertion into an anatomical passageway containing a fluid such as blood. The introducer comprises a needle assembly having a U-wing member and a stylet having a sharpened distal tip. The stylet is attached in fluid communication with the U-wing member such that blood flowing into the stylet may enter the interior of the U-wing member. The introducer further comprises a protective sheath cooperatively engaged to the U-wing member. The protective sheath is movable between a non-operative position whereat the distal tip is exposed and an operative position whereat the distal tip is covered by the sheath. In the preferred embodiment of the present invention, the sheath is separable into two halves when the sheath is in the operative position such that when the needle assembly is separated, the distal tips of the stylet remain covered by the separated sheath. Furthermore, the introducer may include a flashback chamber removably attachable to and in fluid communication with the U-wing member. The flashback chamber allows detection of blood entering the stylet and U-wing member.

The needle assembly of the introducer defines a longitudinal axis and is configured to be separable along such axis. The stylet therefore includes a slit formed along the longitudinal axis for separation thereof. Additionally, a groove may be formed opposite the slit along the longitudinal axis thereof for separation of the stylet. In this respect, the stylet is separable into two halves and each half has a sharpened distal tip that is covered by the sheath when the introducer is separated.

In accordance with the preferred embodiment of the present invention, there is provided a method of using a peelable protected introducer constructed in accordance with the present invention. The method comprises the step of inserting the stylet of the needle assembly into the patient's blood vessel. Next, a catheter is inserted through the stylet into the patient's blood vessel. The stylet is then removed from the patient's blood vessel. As the stylet is being removed, the sheath is advanced from a non-operative position to the operative position such that the distal tip of the stylet is covered. Once the stylet is removed from the patient's blood vessel and the sheath is advanced over the distal tip of the stylet, the U-wing member with stylet is separated into two halves in order to be removed from the catheter. Since the sheath is separable into two halves, the distal tip of the stylet is covered and therefore will not cause inadvertent needle sticks. In the preferred embodiment of the present invention, the flashback chamber is fluidly attached to the U-wing member prior to insertion of the stylet into the patient's blood vessel. After the stylet is inserted into the patient's blood vessel and blood is detected within the flashback chamber, the flashback chamber is removed from the U-wing member such that the catheter can be inserted through the stylet and the patient.

BRIEF DESCRIPTION OF THE DRAWINGS

These as well as other features of the present invention, will become more apparent upon reference to the drawings wherein:

FIG. 4 is a rear exploded view of the introducer shown in FIG. 1;

FIG. 5 is a rear perspective view of the introducer shown in FIG. 1; and

FIG. 6 is a perspective view of the introducer shown in FIG. 1 as divided into two halves.

DETAILED DESCRIPTION OF THE INVENTION

Figures 1, 2, 3:
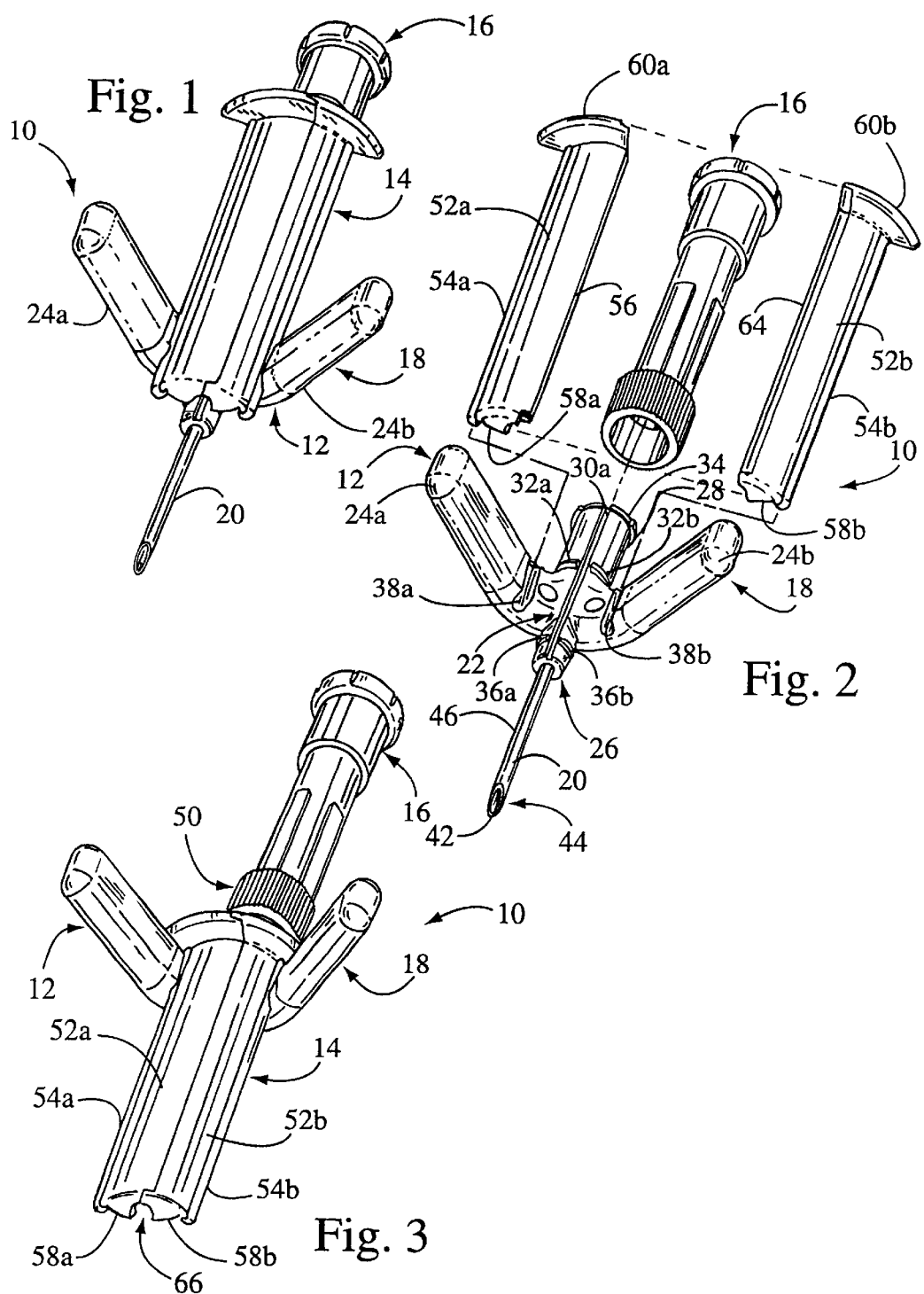
FIG. 1 is a front perspective view of a peelable introducer constructed in accordance with the present invention, illustrating the protective sheath thereof in a non-operative position.
FIG. 2 is a front exploded view of the introducer shown in FIG. 1.
FIG. 3 is a front perspective view of the introducer shown in FIG. 1, illustrating the protective sheath thereof in an operative position.

Referring now to the drawings wherein the showings are for purposes of illustrating a preferred embodiment of the present invention only, and not for purposes of limiting the same, FIG. 1 perspectively illustrates a protected peelable introducer 10 which is insertable into a lumen of an anatomical passageway (e.g. an artery or vein). The introducer 10 comprises a needle assembly 12, a protective sheath 14 and a flashback chamber 16.

NEEDLE ASSEMBLY

The needle assembly 12 of introducer 10 has a U-wing member 18 attached to a sharpened stylet 20 for insertion into an artery or vein of a patient as will be further explained below. As seen in FIG. 2, the U-wing member 18 has a hollow body portion 22 integrally connected to a pair of handle portions 24a, 24b. Each of the handle portions 24a, 24b are bent upwardly from the body portion 22 so as to assume a generally U-shaped configuration that facilitates insertion and splitting of the needle assembly 12, as will be further explained below. Integrally attached to a distal side of the body portion 22 is a distal hub portion 26. The distal hub portion 26 is hollow and fluidly connected to the body portion 22. The U-wing member 18 further includes a hollow proximal connector portion 28 integrally connected to the body portion 22. The proximal connector portion 28 is in fluid communication with the body portion 22 such that fluid can flow through the distal hub portion 26, the body portion 22 and the proximal connector portion 28. As seen in FIG. 2, the distal hub portion 26, the body portion 22 and the connector portion 28 collectively define a longitudinal axis "A" of the needle assembly 12. In the preferred embodiment of the present invention, the U-wing member 18 is fabricated from a plastic type material.

The U-wing member 18 of needle assembly 12 further includes a pair of weakened areas or channels 30a and 30b formed therein as seen in FIGS. 2 and 3. Each of the channels 30a and 30b extend along the U-wing member from the distal hub portion 26 to the proximal connector portion 28. Additionally, each channel 30a, 30b is positioned on the U-wing member 18 such that the U-wing member 18 is divided into two equal halves. In this respect, the U-wing member 18 can be split or divided into two identically configured halves.

The connector portion 28 of the U-wing member 18 includes a pair of proximal shoulders 32a, 32b formed thereon. The proximal shoulders 32a, 32b are slight protuberances formed on the exterior of the U-wing member 18 at the junction between the body portion 22 and the connector portion 28. The proximal shoulders 32a, 32b extend radially relative to longitudinal axis "A" and are disposed on opposite sides of the channels 30a, 30b. In addition, the connector portion 28 of the U-wing member 18 is formed with a flange portion 34 circumferentially surrounding the open proximal end of the connector portion 28. As seen in FIG. 4, each of the channels 30a and 30b are formed within the flange portion 34 such that the flange portion 34 is bisected into two identical halves. The flange portion 34 is configured as a Luer lock in order to couple the flashback chamber 16 to the U-wing member 18, as will be further explained below.

As seen in FIGS. 2 and 4, the distal hub portion 26 includes a pair of distal shoulders 36a, 36b formed thereon that extend radially relative to longitudinal axis "A". The distal shoulders 36a, 36b are slight protuberances disposed on the exterior surface of the hub portion 26 intermediate the distal end of the hub portion 26 and the body portion 22. As seen in FIG. 2, distal shoulders 36a, 36b are disposed on opposite sides of the channels 30a, 30b.

Each handle portion 24a and 24b includes a rail groove 38a, 38b integrally formed therein. As seen in FIG. 2, each rail groove 38a, 38b is formed within an inner side of a respective handle portion 24a, 24b. In other words, each rail groove 38a, 38b is formed on sides of the handle portions 24a, 24b that are facing each other. Each rail groove 38a, 38b extends in parallel, spaced relation to the longitudinal axis "A" of the U-wing member 18. Each rail groove 38a, 38b is sized to receive and support the protective sheath 14 as will be further explained below.

As seen in FIG. 4, each of the handle portions 24a, 24b includes a sheath locking notch or recess 48a, 48b disposed on a proximal side thereof. Each locking recess 48a, 48b is integrally formed within a respective handle portion 24a, 24b and sized to receive the protective sheath 14 as will be further explained below.

In order to insert the needle assembly 12 into the patients vein or artery, a stylet 20 is attached to the hub portion 26 of U-wing member 18. The stylet 20 may be insert molded or attached with an adhesive and/or press fit to the hub portion 26. The stylet 20 has a lumen 42 extending axially between a distal tip 44 and the hub portion 26. In this respect, the lumen 42 of stylet 20 is in fluid communication with the hollow body portion 22 and proximal connector portion 28 of U-wing member 18. Furthermore, the lumen 42 of stylet 20 is coaxially aligned with longitudinal axis "A".

The stylet 20 is fabricated by rolling a planar section of metallic material into a substantially closed "C" cross-sectional configuration. In this respect, a slit 46 is formed in stylet 20 in substantially parallel spaced relation to longitudinal axis "A". As will be recognized to those of ordinary skill in the art, the stylet 12 may be alternatively fabricated from a segment of tubing having a circular cross-sectional configuration, with the slit 46 being formed therein by removing a linear section of material with a laser from along the longitudinal axis defined by such tubing segment. Furthermore, the stylet 20 may be formed with a generally U-shaped groove (not shown) disposed about 180° form the slit 46 along the longitudinal axis "A". The groove may be formed by scoring the outside surface of the stylet 20 with a laser or perforating the stylet 20 during the manufacture thereof. The distal tip 44 of stylet 20 is formed as a sharpened, beveled distal tip that is advanceable into the patient's vein or artery.

FLASHBACK CHAMBER

The needle assembly 12 is fluidly attachable to the flashback chamber 16. The flashback chamber 16 is a cylindrical hollow chamber that is typically translucent in order to view fluids flowing therein. In this respect, the flashback chamber 16 includes a coupling portion 50 containing Luer threads therein. The Luer threads are engageable to the flange portion 34 of the proximal connector portion 28. As such, the flashback chamber 16 is fluidly attachable to the U-wing member 18 through connector portion 28. Fluids flowing through the U-wing member 18 can therefore enter the interior of the flashback chamber 16. Disposed on the end of the flashback chamber 16 opposite the coupling portion 50 is a vent 43. The vent 43 allows air, but not liquids, to escape from the interior of the flashback chamber 16.

PROTECTIVE SHEATH

The protective sheath 14 prevents inadvertent needle sticks by enclosing the distal tip 44 of the stylet 20 after use. The protective sheath 14 has an elongate, arcuate first section 52a coupled to an elongate, arcuate second section 52b. Each section 52a, 52b is preferably fabricated from a plastic material and sized to cover the stylet 20 when in an operative position, as will be further explained below. As seen in FIG. 2, the first section 52a has a first rail 54a extending between the distal and proximal ends on an outer side thereof. Disposed on an inner, opposite side of the first section 52a is a mating groove 56 extending between the distal and proximal ends thereof. As seen in FIG. 2, the first section 52a includes a first distal locking tab 58a formed on the distal end thereof and extending in generally perpendicular relation thereto. The first section 52a additionally includes a first cover face 60a formed on the proximal end thereof. The first cover face 60a is integrally formed with the first section 52a and extends generally perpendicularly or radially relative thereto. The first cover face 60a includes a first proximal locking tab portion 62a formed on a lower side thereof, as seen in FIGS. 4 and 5.

The second section 52b of the protective sheath 14 is similar to the first section 52a. In this respect, the second section 52b includes a second rail 54b extending between the distal and proximal ends of an outer side of the second section 52b. Disposed on an inner, opposite side of the second section 52b is a mating tongue 64 that is cooperatively engageable to the mating groove 56 of the first section 52a, as will be further explained below. The second section 52b includes a second distal locking tab 58b integrally formed on the distal end thereof and extending in generally perpendicular relation thereto. A second cover face 60b is integrally formed on the proximal end of the second section 52b. The second cover face 60b extends generally perpendicularly or radially relative to the second section 52b. The second cover face 60b includes a second proximal locking tab portion 62b formed on a lower side thereof, as seen in FIGS. 4 and 5.

The first and second sections 52a, 52b collectively function as the protective sheath 14 when inserted into the U-wing member 18. As seen in FIG. 1, the first section 52a is coupled to the second section 52b when rails 54a, 54b are inserted into respective ones of the rail grooves 38a, 38b of the U-wing member 18. The protective sheath 14 defined by the first and second sections 52a, 52b has a generally semi-circular configuration. The distal locking tabs 58a, 58b collectively define a generally semicircular opening 66 on the sheath 14 when the first and second sections 52a, 52b are attached to one another. Additionally, the first and second cover faces 60a, 60b collectively define a finger push region 68 of the sheath 14 when the first and second sections 52a, 52b are coupled together.

MODE OF OPERATION

In order to use the introducer 10, the sheath 14 is cooperatively engaged to the U-wing member 18. The protective sheath 14 is positioned on the U-wing member such that the distal locking tabs 58a, 58b of the sheath 14 are disposed between the stylet 20 and the distal shoulders 36a, 36b. Typically, as seen in FIG. 1, the distal locking tabs 58a, 58b are positioned adjacent to the distal side of the distal shoulders 36a, 36b. In this nonoperative position, the sheath 14 does not obstruct the stylet 20 such that the stylet 20 can be advanced into a blood vessel of a patient. The stylet 20 is advanced until blood flashing back distally from the patient's blood vessel is evidenced within flashback chamber 16. Once blood is visible, the flashback chamber 16 is removed from the U-wing member 18. Next, a catheter may be inserted into the interior of the U-wing member 18. The stylet 20 facilitates advancement of the catheter into the patient's blood vessel and proper positioning of such within the patient's body. Once the catheter has been properly positioned, the introducer 10 is distally removed from the blood vessel.

During removal of the introducer 10, the sheath 14 is distally advanced into an operative position, as seen in FIG. 3. The sheath 14 is advanced by applying distally directed pressure to the push region 68 with the technician's finger. The distal end of the sheath 14 covers or encloses the sharpened distal tip 44 in order to protect the health care worker from inadvertent needle sticks. The opening 66 of sheath 14 allows the sheath 14 to be advanced over the catheter and stylet 20 when advanced into the operative position.

The sheath 14 is locked into place over the stylet 20 by proximal locking tab portions 62a, 62b snapping over proximal shoulders 32a, 32b. When the sheath 14 is fully advanced over the distal tip 44 of stylet 20, the first and second cover faces 60a, 60b engage respective ones of the locking recesses 48a, 48b. Each locking recess 48a, 48b is sized to receive a respective cover face 60a, 60b when the sheath 14 is fully advanced over the stylet 20 and the proximal locking tab portions 62a, 62b have been snapped over a respective proximal shoulder 32a, 32b. In this respect, each proximal shoulder 32a, 32b is disposed adjacent to a respective one of the first and second handle portions 24a, 24b such that the proximal shoulders 32a, 32b provide a forwarding biasing force for the sheath 14 against the handle portions 24a, 24b.

Next, the introducer 10 is removed from the catheter by tearing the needle assembly 12 along longitudinal axis "A". Specifically, since channels 30a, 30b form weakened portions along U-wing member 18, the needle assembly 12 can be torn or split into two halves by bending the first and second handle portions 24a, 24b away from each other. Since the stylet 20 is formed with a slit 46 and a scored U-shaped groove on the opposite side thereof, the stylet 20 is additionally separable into two sections. Additionally, since the sheath 14 is formed from two separate members (i.e., first section 52a and second section 52b), sheath 14 is separated into two halves along mating groove 56 and mating tongue 64.

After separation of the introducer 10 into two halves, the distal tip 44 of each half of the stylet 20 is protected after the needle assembly 12 is separated. Since, each section 52a, 52b of sheath 14 is maintained in position with a respective cover face 60a, 60b, both the first and second sections 52a, 52b will be prevented from rotating and be maintained in a position that covers the distal tip 44 of stylet 20 after separation thereof. Therefore as seen in FIG. 6, the introducer 10 is separable into two halves whereby each half of the stylet 20 is protected by a respective one of the first and second sections 52a, 52b. In this respect, after separation, the introducer 10 can be properly disposed without the risk of inadvertent needle sticks to the health care worker.

Additional modifications and improvements of the present invention may also be apparent to those of ordinary skill in the art. Thus, the particular combination of parts described and illustrated herein is intended to represent only certain embodiments of the present invention, and is not intended to serve as limitations of alternative devices within the spirit and scope of the invention.

What is claimed is:

1. A protected peelable introducer comprising:

a needle assembly having:

a U-wing member; and a stylet in fluid communication with the U-wing member and defining a sharpened distal tip wherein the needle assembly defines a longitudinal axis and is configured to be separable along the longitudinal axis thereof; and a protective sheath cooperatively engaged to the U-wing member and movable relative thereto from a non-operative position whereat the distal tip is exposed to an operative position whereat the distal tip is covered by the sheath;

wherein the needle assembly and the sheath are separable into two halves when the sheath is in the operative position.

2. The introducer of claim 1 further comprising a flashback chamber removably attachable to and in fluid communication with the U-wing member.

3. The introducer of claim 2 wherein the stylet of the needle assembly includes a slit formed thereon to facilitate the separation thereof along the longitudinal axis.

4. The introducer of claim 3 wherein the stylet is separable into two halves and each half has a sharpened distal tip.

5. A method of using a peelable protected introducer having U-wing member, a stylet in fluid communication with the U-wing member and having a sharpened distal tip, and a protective sheath cooperatively engaged to the U-wing member and movable between a non-operative position wherein the distal tip is exposed and an operative position wherein the distal tip is covered by the sheath, the method comprising the steps of:

a) inserting the stylet into a patient's blood vessel;

b) inserting a catheter through the stylet into the patient's blood vessel;

c) removing the stylet from the patient's blood vessel;

d) advancing the sheath into the operative position;

e) separating the stylet, the U-wing member and the sheath such that the ends of the stylet are enclosed by the sheath after separation thereof.

6. The method of claim 5 wherein prior to step (a) the sheath is advanced into the non-operative position.

7. The method of claim 5 wherein the introducer further comprises a flashback chamber and step (a) comprises:

(1) fluidly attaching the flashback chamber to the U-wing member;

(2) inserting the stylet into the patient's blood vessel;

(3) detecting the patient's blood within the flashback chamber; and (4) removing the flashback chamber from the U-wing member.

* * * * *